(12) United States Patent
Gong et al.

(10) Patent No.: US 11,191,546 B2
(45) Date of Patent: Dec. 7, 2021

(54) LEFT ATRIAL APPENDAGE OCCLUDER AND FABRICATING METHOD THEREFOR

(71) Applicant: Shanghai Push Medical Device Technology Co., Ltd., Shanghai (CN)

(72) Inventors: Shanshi Gong, Shanghai (CN); Rui Li, Shanghai (CN)

(73) Assignee: SHANGHAI PUSH MEDICAL DEVICE TECHNOLOGY CO., LTD.

( * ) Notice: Subject to any disclaimer, the term of this patent is extended or adjusted under 35 U.S.C. 154(b) by 385 days.

(21) Appl. No.: 16/081,171

(22) PCT Filed: Aug. 11, 2016

(86) PCT No.: PCT/CN2016/094588
§ 371 (c)(1),
(2) Date: Oct. 5, 2018

(87) PCT Pub. No.: WO2017/148102
PCT Pub. Date: Sep. 8, 2017

(65) Prior Publication Data
US 2019/0046213 A1    Feb. 14, 2019

(30) Foreign Application Priority Data

Mar. 3, 2016   (CN) .......................... 201610117939.5
Jul. 18, 2016  (CN) .......................... 201610565731.X

(51) Int. Cl.
*A61B 17/12*      (2006.01)
*A61B 17/00*      (2006.01)

(52) U.S. Cl.
CPC ........ *A61B 17/12122* (2013.01); *A61B 17/12* (2013.01); *A61B 17/1214* (2013.01);
(Continued)

(58) Field of Classification Search
CPC ........ A61B 17/12122; A61B 17/12172; A61B 17/12031
See application file for complete search history.

(56) References Cited

U.S. PATENT DOCUMENTS 9,808,253 B2 *   11/2017  Li ................... A61B 17/12122
10,624,648 B2 *   4/2020  Li ....................... A61B 17/0057
(Continued)

FOREIGN PATENT DOCUMENTS

CN       202143640 U      2/2012
CN       102805654 A     12/2012
(Continued)

*Primary Examiner* — Sarah A Simpson
(74) *Attorney, Agent, or Firm* — Global IP Services; Tianhua Gu

(57) ABSTRACT

A left atrial appendage occluder and a fabricating method thereof are provided. The left atrial appendage occluder includes a plugging column and a anchor located on the plugging column, wherein the plugging column is woven from an elastic metal wire, or woven from an elastic metal wire and an elastic metal sheet, the anchor is made by partially flattening and then cutting the elastic metal wire, or the anchor is made by cutting the elastic metal sheet. In the above-described left atrial appendage occluder, firstly, the anchor is formed on the elastic metal wire and/or the elastic metal sheet, and then the elastic metal wire and/or the elastic metal sheet with the anchor are/is co-woven with other elastic metal wire to form the plugging column of the left atrial appendage occluder. Therefore, the amount of the anchor is not limited, and a plurality of anchors can be provided.

11 Claims, 8 Drawing Sheets

(52) U.S. Cl.
CPC .. *A61B 17/12172* (2013.01); *A61B 17/12177* (2013.01); *A61B 17/12031* (2013.01); *A61B 2017/00526* (2013.01); *A61B 2017/00867* (2013.01)

(56) References Cited

U.S. PATENT DOCUMENTS

| | | |
|---|---|---|
| 2011/0208233 A1 | 8/2011 | McGuckin, Jr. et al. |
| 2013/0131717 A1* | 5/2013 | Glimsdale ........ A61B 17/12122 606/213 |
| 2015/0133989 A1* | 5/2015 | Lubock .............. A61B 17/0057 606/200 |
| 2016/0022419 A1* | 1/2016 | Yellin ................... A61F 2/2466 623/2.11 |

FOREIGN PATENT DOCUMENTS

| | | |
|---|---|---|
| CN | 204246182 U | 4/2015 |
| CN | 204318826 U | 5/2015 |
| CN | 104918559 A | 9/2015 |
| CN | 104958087 A | 10/2015 |
| CN | 105662516 A | 6/2016 |

\* cited by examiner

LEFT ATRIAL APPENDAGE OCCLUDER AND FABRICATING METHOD THEREFOR

CROSS REFERENCE TO RELATED PATENT APPLICATION

The present application is the US national stage of PCT/CN2016/094588 filed on Aug. 11, 2016, which claims the priorities of the CN2016101179395 filed on Mar. 3, 2016 and CN201610565731X filed on Jul. 18, 2016, which applications are incorporated herein by reference.

BACKGROUND OF THE PRESENT INVENTION

Field of Invention

The present invention relates to a novel medical device. The medical device is an occluder to be delivered to a human body via a catheter technique using an interventional method, to prevent strokes caused by left atrial appendage thrombosis due to atrial fibrillation.

The present invention particularly relates to a left atrial appendage occluder.

The present invention further particularly relates to a fabricating method of a left atrial appendage occluder.

Description of Related Arts

Atrial fibrillation (AF) is the most common perpetual arrhythmia, the symptoms are characterized by irregular heartbeats, atrial fibrillation may lead to thrombus, stroke, heart failure, and other complications which may result in serious consequences. Non-valvular atrial fibrillation is a high-incidence type of atrial fibrillation. In non-valvular atrial fibrillation, 90% or more of thrombosis is associated with left atrial appendage. The incidence of atrial fibrillation in the general population is 0.5% to 1.5%.

There are 33.50 million patients with atrial fibrillation worldwide, and there are about 8 million patients with atrial fibrillation in China. The risk of stroke in patients with atrial fibrillation is five times that in the average people. In China, stroke is the leading cause of death and the leading cause of disease burden. Strokes caused by atrial fibrillation usually have more severe clinical manifestations and higher mortality, and are more likely to relapse.

The left atrial appendage is a remnant of the original left atrium during the embryonic period. It has a narrow and curved tubular shape, has a narrow and pointed top, and has abundant pectinate muscles and trabecular muscles therein. When atrial fibrillation occurs, an entrance of the left atrial appendage is obviously widened, and the effective regular contraction is lost. It is difficult for the inward movement of the auricle wall to leads to sufficient emptying of the left atrial appendage, which will result in blood deposition in the left atrial appendage, and further form the pathological basis of the thrombus. The morphological characteristics of the left atrial appendage per se are likely to cause blood flow to form vortex and slow down the flow rate, which is also a condition for promoting thrombosis.

Anticoagulant therapy is a basic treatment for preventing stroke in patients with atrial fibrillation. However, some patients may suffer from intolerance, bleeding events, compliance and the like when taking anticoagulants, and the patients also need to frequently go back to a hospital for examination and adjusting the dose. Catheter radiofrequency ablation is one of the treatments for paroxysmal atrial fibrillation and persistent atrial fibrillation.

Left atrial appendage occlusion is used to prevent the formation of a thrombus in the left atrial appendage during atrial fibrillation by occluding the left atrial appendage, thereby reducing the risk of long-term disability or death caused by thromboembolism in patients with atrial fibrillation. Various technical devices have been developed and used for left atrial appendage occlusion. The details are as follows:

A left atrial appendage occluder is a nickel-titanium cage structure which is formed by heat treatment after laser-cutting a nickel-titanium hollow tube, wherein an outer part of the nickel-titanium cage structure is covered with a layer of polyester fiber membrane. The left atrial appendage occluder further includes a plurality of anchors, and tips of the anchors face a proximal end of the left atrial appendage occluder to attach the left atrial appendage occluder to an inner wall of the left atrial appendage. The left atrial appendage occluder having the above structure may be a cage-type left atrial appendage occluder disclosed in the specification of Chinese Patent Application No. 201410672016.7. However, the left atrial appendage occluder of the foregoing structure has the following drawbacks:

1. Since the cage structure is sparse, the fitting property between a plugging column and the inner wall of the left atrial appendage is poor, which will affect the stability of the plugging column in the left atrial appendage. In addition, this sparse structure has a large pressure on the left atrial appendage, which is likely to damage the left atrial appendage and cause pericardial tamponade.

2. Since the anchors of the cage structure are cut on skeletons of the cage structure, the number of anchors is related to the number of skeletons of the cage. The number of the skeletons of the cage is generally 8-10, so the number of the anchors is generally 8-10. The number of the anchors is limited by the structure of the cage, which affects the fixation effect of the occluder in the left atrial appendage. If it is necessary to increase the number of the anchors, the number of the skeletons of the cage needs to be increased, which will weaken the strength of the skeleton structure of the cage and reduce the supporting force of the cage, resulting in that the cage is relatively "soft" and does not meet the requirements for use.

3. Anchors for attaching the left atrial appendage occluder to the inner wall of the left atrial appendage are cut out on the surface of the cage, and therefore the anchors are hard. In addition, the tip of anchors faces the proximal end of the left atrial appendage occluder, and the bottom end of anchors (that is, a connection end connected to the cage) faces the distal end of the left atrial appendage occluder, therefore, the left atrial appendage occluder with the cage structure can only be pushed and pulled once, and cannot be pushed and pulled repeatedly. The specific reason is: Anchors are attached to the cage of the left atrial appendage occluder by using a special device, after the left atrial appendage occluder is delivered into a human body by using a delivery device and released, the left atrial appendage occluder is successfully attached to the inner wall of the left atrial appendage under the action of anchors. If it is necessary to adjust the position of the left atrial appendage occluder or take out the left atrial appendage occluder, the left atrial appendage occluder first need to be collected in the delivery device, and then the corresponding operation is performed. As shown in FIG. 1a and FIG. 1b, during the process of collecting the left atrial appendage occluder into the sheath, the proximal end of the left atrial appendage occluder is firstly leftwards collected into the sheath, followed by anchors 100 and the distal end of the left atrial appendage occluder. Consequently, during the process of being collected into the sheath, anchors 100 are completely bent rightwards and attached to a peripheral surface of the cage 200, and thus the deformation of the bottom ends 300 of anchors 100 are very large. Therefore, after the left atrial appendage occluder is pushed out of the sheath again, the tip of anchors 100 cannot completely return to its original position. As shown in FIG. 1a and FIG. 1c, the tip of anchors 100 face the distal end of the left atrial appendage occluder and cannot return to its original state of facing the proximal end of the left atrial appendage occluder, causing anchors 100 to lose the function of attaching the left atrial appendage occluder to the inner wall of the left atrial appendage. In other words, the left atrial appendage occluder cannot be anchored again in the left atrial appendage, so that the left atrial appendage occluder can only be pushed and pulled once, and cannot be pushed and pulled repeatedly.

Another left atrial appendage occluder includes an umbrella structure covered by a polytetrafluoroethylene membrane, and also made from a nickel-titanium tube. This device also includes anchors for fixing the left atrial appendage occluder to the inner wall of left atrial appendage. However, this left atrial appendage occluder has a problem that improper size can result in prolonged implantation time or reduced efficiency.

Another left atrial appendage occluder for occluding left atrial appendage is a nickel-titanium mesh woven structure. Anchors are easily formed by a nickel-titanium wires after being bent, and is fixed on the inner wall of the left atrial appendage. As the device adopts the nickel-titanium wires as the anchors, the fixing firmness is relatively poor, and the occluder is likely to fall off.

Thus, the disadvantages of the left atrial appendage occluder in the prior art may result in longer operation time, incomplete occlusion of the left atrial appendage, compression of the coronary artery, severe complications resulting from removal of the device from the left atrial appendage, or the like. In addition, the conventional left atrial appendage occluder is too large, which may potentially cause left atrial appendage stretching. For example, the conventional left atrial appendage occluder may be too large up to 20-25%, and the left atrial appendage occluder stretching may cause ulceration or arrhythmia.

To this end, the present invention provides a novel left atrial appendage occluder for occluding the "left atrial appendage" which is the root cause of thrombosis in patients with atrial fibrillation, thereby reducing the risk of stroke in patients with atrial fibrillation.

SUMMARY OF THE PRESENT INVENTION

In view of the foregoing disadvantages of the prior art, an object of the present invention is to provide a left atrial appendage occluder which can increase the number of anchors to improve fitting property between the left atrial appendage occluder and the left atrial appendage while ensuring the structural strength of the left atrial appendage occluder.

In order to achieve the foregoing object, the present invention provides a left atrial appendage occluder comprising a plugging column and anchors located on the plugging column, wherein the plugging column is woven from an elastic metal wire, or woven from an elastic metal wire and an elastic metal sheet, the anchors are made by partially flattening and then cutting the elastic metal wire, or the anchors are made by cutting the elastic metal sheet. Therefore, when the plugging column is woven from the elastic metal wire, the anchors are formed on the elastic metal wire; when the plugging column is woven from the elastic metal wire and the elastic metal sheet, the anchors may be formed only on the elastic metal sheet, or formed only on the elastic metal wire, or formed on both the elastic metal sheet and the elastic metal wire.

Preferably, the anchors are made by partially flattening and then laser-cutting the elastic metal wire, or the anchors are made by laser-cutting the elastic metal sheet.

Further, the elastic metal wire and/or the elastic metal sheet are/is cut to form an cutting groove, the anchor is bent and extends from the proximal end of the cutting groove, and the tip of the anchors faces the proximal end of the left atrial appendage occluder.

Preferably, the length of the anchors ranges from 1 mm to 4 mm.

Further, the tip of the anchors is further provided with a drag reducing hook portion; and when the left atrial appendage occluder is collected into a delivery system, the drag reducing hook portion of the anchor is in line contact with an inner wall of a sheath in the delivery system.

Further, a cover disk connected to the plugging column and a blood flow blocking membrane for blocking blood flow are further comprised, and the blood flow blocking membrane is flatly fixed in the cover disk and the plugging column.

Preferably, the plugging column is cylindrical, and two ends of the plugging column are respectively constrained and fixed by a distal gathering point and an intermediate gathering point; and the cover disk is a flat disk, and two ends of the cover disk are respectively constrained and fixed by the intermediate gathering point and a proximal gathering point.

Preferably, the elastic metal wire is a nickel-titanium alloy metal wire, and the elastic metal sheet is a nickel-titanium alloy metal sheet.

Further, the proximal gathering point, the intermediate gathering point and the distal gathering point each comprise an inner steel sleeve and an outer steel sleeve, end parts of a plurality of elastic metal wires are located in the inner steel sleeve or located between the inner steel sleeve and the outer steel sleeve, the plurality of elastic metal wires is tightly matched and fixed with the inner steel sleeve, and the inner steel sleeve is fixed with the outer steel sleeve.

Preferably, an inner wall of a proximal end of the inner steel sleeve or an inner wall of a proximal end of the outer steel sleeve of the proximal gathering point is provided with a connecting thread, and the connecting thread is used for connecting the left atrial appendage occluder and a push rod in a delivery system.

Preferably, an outer wall of a proximal end of the outer steel sleeve of the proximal gathering point has a frustum shape.

Further, a proximal end of the plugging column is provided with a first region recessed inward, the intermediate gathering point is embedded in the first region of the plugging column, and a proximal end of the intermediate gathering point is located at a distal side of the proximal end of the plugging column.

Further, the proximal gathering point is completely embedded in the cover disk, and a tail end of the proximal gathering point is flush with a plane of the cover disk.

Another object of the present invention is to provide a manufacturing method for processing a left atrial appendage occluder as described above, comprising the following steps in sequence:

1) partially flattening one or more elastic metal wires to form a flattened surface on the elastic metal wire;

2) cutting an edge contour of anchors on the flattened surface of the elastic metal wire;

3) bending the anchors outward from the elastic metal wire;

4) performing heat-treatment on the elastic metal wire to shape the anchors;

5) weaving the elastic metal wire with the anchor and other elastic metal wires into a plugging column, and locating the anchors on a peripheral surface of the plugging column; and 6) placing the plugging column into a mould and performing heat-treatment for shaping.

Another object of the present invention is to provide a fabricating method for processing a left atrial appendage occluder as described above, comprising the following steps in sequence:

a) cutting an edge contour of anchors on one or more flat elastic metal sheets, the elastic metal sheets forming a flattened surface;

b) bending the anchors outward from the elastic metal sheet;

c) performing heat-treatment on the elastic metal sheet to shape the anchors;

d) weaving the elastic metal sheet and a plurality of elastic metal wires into a plugging column, and locating the anchors on a peripheral surface of the plugging column; and e) placing the plugging column into a mould and performing heat-treatment on for shaping.

As described above, the left atrial appendage occluder and the fabricating method thereof provided in the present invention have the following beneficial effects:

In the foregoing left atrial appendage occluder, the anchors are first processed on the elastic metal wire and/or the elastic metal sheet, and then the elastic metal wire and/or the elastic metal sheet with the anchors are co-woven with other elastic metal wires to form the plugging column of the left atrial appendage occluder. Therefore, the number of the anchors is not limited, and a plurality of anchors can be provided, so that after the left atrial appendage occluder is implanted in the human body, the pressure of the tip of the anchors is smaller, the damage to the left atrial appendage is smaller, and the fitting property between the left atrial appendage occluder and the left atrial appendage is improved. Meanwhile, the supporting force of the plugging column is also improved, and the structural strength of the left atrial appendage occluder is ensured to meet the actual demand. Further, both the bottom end and the tip of the anchor face the proximal end of the left atrial appendage occluder, so that during the process of pushing and pulling the left atrial appendage occluder by using the delivery system, the anchors can be returned to the state before bending along a direction of pulling the left atrial appendage occluder into the sheath. Therefore, the deformation or the bending of the bottom end of the anchor is very small, and thus the left atrial appendage occluder can be pushed and pulled for a plurality of times. Meanwhile, since the anchors are integrated, the anchor is not likely to fall off. Therefore, the left atrial appendage occluder can be firmly and reliably attached to the inner wall of the left atrial appendage.

BRIEF DESCRIPTION OF THE DRAWINGS

FIG. 1 is a state diagram of a anchor during a process of pushing and pulling a cage-type left atrial appendage occluder in the prior art, wherein FIG. 1a is a schematic diagram of a relationship between the anchor and a cage after the cage-type left atrial appendage occluder is anchored on an inner wall of left atrial appendage;

FIG. 1b is a schematic diagram of a relationship between the anchor and the cage after the cage-type left atrial appendage occluder is collected into a sheath for a second time; and FIG. 1c is a schematic diagram of a relationship between the anchor and the cage after the cage-type left atrial appendage occluder is pushed out from the sheath.

b) is a state diagram when the anchor in the left atrial appendage occluder according to the fifth embodiment is partially collected into the sheath; and c) is a state diagram when the anchor in the left atrial appendage occluder according to the fifth embodiment is completely collected into the sheath.

Figure 19:
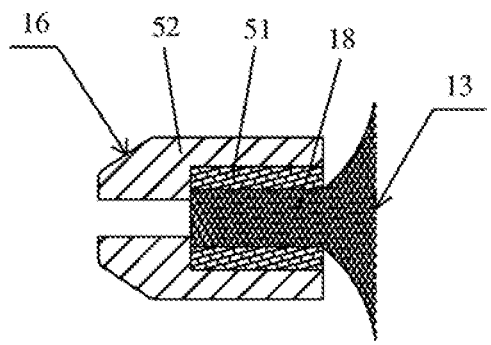

FIG. 19 is a schematic diagram of connection of a proximal gathering point and an elastic metal wire in a cover disk in this application.

Figure 20:
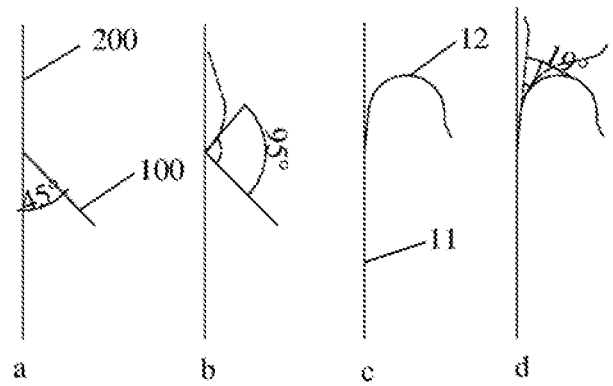
Figure 21:
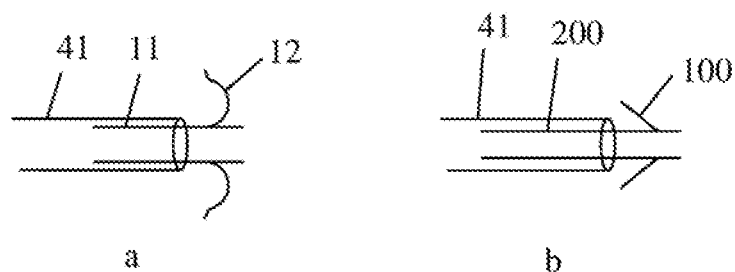
Figure 22:
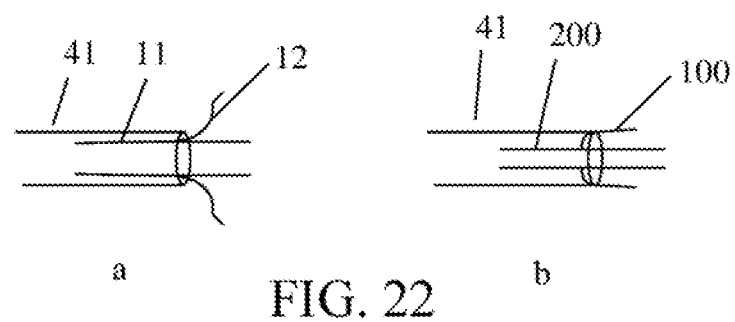
Figure 23:
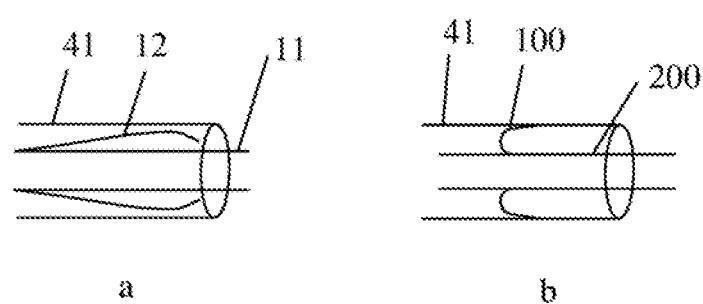
Figure 24:
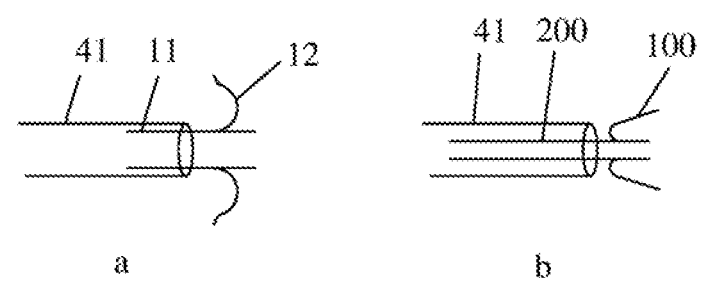

FIG. 20 is a comparison diagram of deformation states of anchors on a left atrial appendage occluder in this application and on a cage-type left atrial appendage occluder in the prior art when the left atrial appendage occluder is collected into a sheath.

FIG. 21 to FIG. 24 are comparison diagrams of deformation states of anchors on a left atrial appendage occluder in this application and on a cage-type left atrial appendage occluder in the prior art when the left atrial appendage occluder is collected into a sheath and after the left atrial appendage occluder is released from the sheath.

Figure 25:
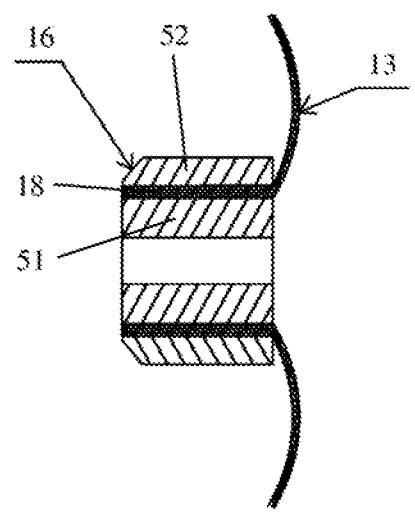
Figure 26:
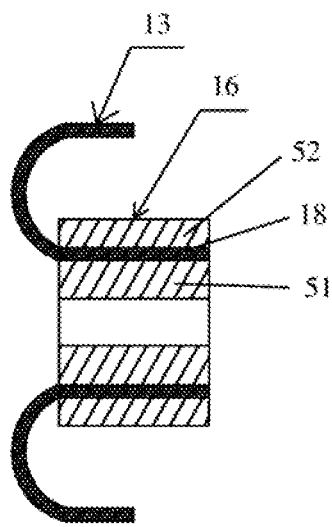

FIG. 25 and FIG. 26 respectively show different embodiments of a connection structure of a proximal gathering point and an elastic metal wire in a cover disk in this application.

REFERENCE NUMERALS 10, 20, 30, 40, 50: Left atrial appendage occluder
11: Plugging column
12: Anchor
121: Drag reducing hook portion
122: Opening
123: Anchoring portion
124: Curved portion
125: Cutting groove
13: Cover disk
14: Distal gathering point
15: Intermediate gathering point
16: Proximal gathering point
17: Blood flow blocking membrane
18: Elastic metal wire
21: Elastic metal sheet
31: Proximal anchor
32: Distal anchor
41: Sheath
42: Push rod
51: Inner steel sleeve
52: Outer steel sleeve
61: Flattened surface

DETAILED DESCRIPTION OF THE PREFERRED EMBODIMENTS

The implementations of the present invention are described in the following by using specific embodiments, and those skilled in the art can readily appreciate other advantages and effects of the present invention from content disclosed in this specification.

It is to be understood that the structures, the proportions, the sizes, and the like as drawn in the accompanying drawings of this specification are only used to corporate with the content disclosed in this specification in order to facilitate the understanding and reading of those skilled in the art, and are not intended to limit the conditions under which the present invention can be implemented, and thus are not technically meaningful. Any modification of the structure, change of the proportional relationship or adjustment of the size without affecting the obtainable effects and the achievable purposes of the present invention should fall within the scope of the technical content disclosed by the present invention. In the meantime, the terms such as "upper", "lower", "left", "right", "intermediate", "one" and the like used in this specification are also for convenience of description, and are not intended to limit the enforceable scope of the present invention. The change or adjustment of the relative relationship is also considered to be within the enforceable scope of the present invention in the absence of substantial changes in the technical content.

In the following embodiments, a proximal end described below refers to an end of a left atrial appendage occluder near an operator, and a distal end described below refers to an end of the left atrial appendage occluder away from the operator.

This application provides a left atrial appendage occluder for occluding left atrial appendage. Meanwhile, the left atrial appendage occluder can be pulled into a line shape, and implanted into left atrial appendage in a human body via a delivery device through a blood vessel of a patient by using a minimally invasive therapy. Occluding the left atrial appendage can prevent the thrombosis in the left atrial appendage of patients with atrial fibrillation, thereby reducing the risk of long-term disability or death due to thromboembolism in the patients with atrial fibrillation. Meanwhile, occluding the left atrial appendage by the left atrial appendage occluder can eliminate the long-term dependence of the patients with atrial fibrillation on anticoagulants and provide the patients with new treatment options. Four preferred embodiments of the left atrial appendage occluder are provided below.

First Embodiment

Figure 1:
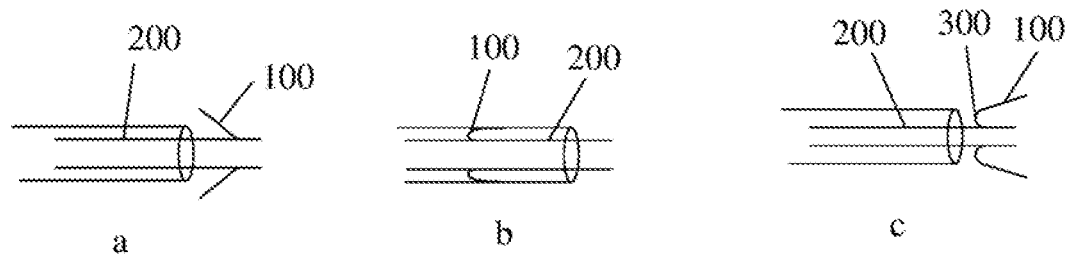
Figure 2:
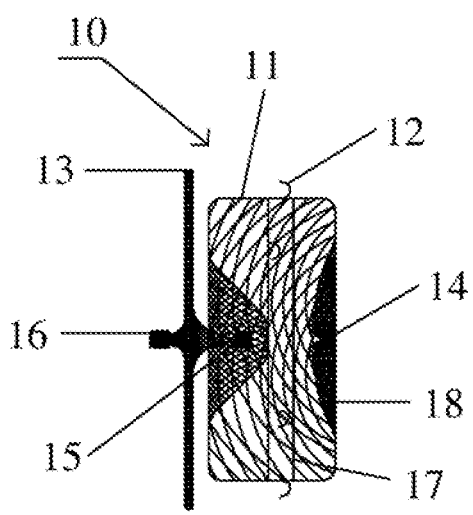
FIG. 2 is a front view of a first embodiment of a left atrial appendage occluder in the present invention.

As shown in FIG. 2, a left atrial appendage occluder 10 according to the first embodiment comprises a plugging column 11 having a proximal end and a distal end. Seen in a direction shown in FIG. 2, a left end of the plugging column 11 is the proximal end of the plugging column 11, and a right end of the plugging column 11 is the distal end of the plugging column 11. The plugging column 11 is woven from an elastic metal wire 18, and the elastic metal wire 18 is partially forged (that is, partially flattened) and then laser-cutting to form a flattened surface 61 with a flat. The flattened surface 61 is provided with anchors 12 bent and extending outwardly and formed on a peripheral surface of the plugging column 11. In other words, the anchor 12 is made by partially forging and then laser-cutting the elastic metal wire 18, so that the peripheral surface of the plugging column 11 is provided with a plurality of anchors 12, and the plurality of anchors 12 being used for anchoring the plugging column 11 on an inner wall of left atrial appendage. In addition, the partial forging described in this application is partial flattening, and thus the flattened surface 61 is a flat portion formed on the elastic metal wire 18 after the elastic metal wire 18 is partially flattened.

Figure 4:
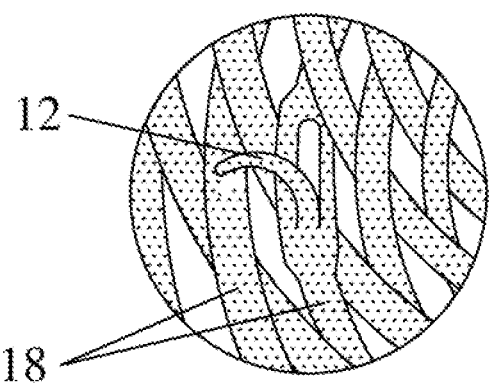
FIG. 4 is a partial enlarged view of a plugging column and a anchor on the left atrial appendage occluder according to the first embodiment.
Figure 5:
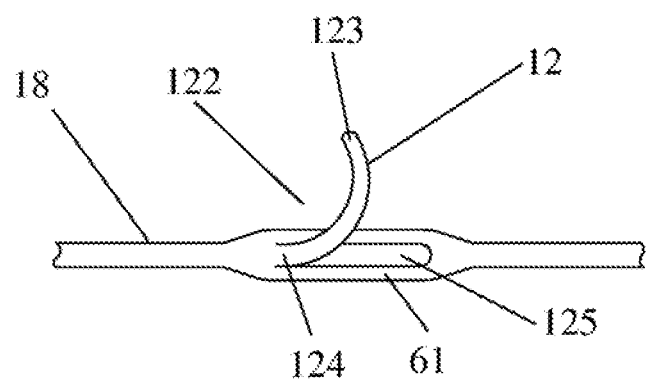
FIG. 5 is a state diagram of the anchor after an elastic metal wire on the left atrial appendage occluder according to the first embodiment is subjected to partial forging and laser-cutting sequentially.

A fabricating method for processing the left atrial appendage occluder 10 according to the first embodiment comprises the following steps in sequence:

1) as shown in FIG. 5, partially flattening one or more first elastic metal wires, that is, partially flattening the first elastic metal wire to form the flattened surface 61 on the first elastic metal wire;

2) as shown in FIG. 5, laser-cutting an edge contour of the anchor 12 on the flattened surface 61 of the first elastic metal wire;

3) as shown in FIG. 5, bending the anchor 12 outward from the first elastic wire, wherein a tip of the anchor 12 has an anchoring portion 123, a bottom end of the anchor 12 has a curved portion 124, and the anchor 12 is connected to the flattened surface 61 by using the curved portion 124 as a transitional bend;

4) performing heat-treatment to the first elastic metal wire to shape the anchor 12;

5) as shown in FIG. 2 and FIG. 4, weaving the first elastic metal wire and a plurality of second elastic metal wires into the plugging column 11, and locating the anchor 12 on a peripheral surface of the plugging column 11, so that the plugging column 11 is woven by a plurality of elastic metal wires 18, that is, the first elastic metal wire and the second elastic metal wires together constitute a plurality of elastic metal wires 18 for weaving the plugging column 11; and 6) placing the plugging column 11 into a mould, and performing heat-treatment for shaping, so as to shape the plugging column 11.

In the above left atrial appendage occluder, the anchor 12 is first processed on the elastic metal wire 18, and then the elastic metal wire 18 with the anchor 12 are co-woven with other elastic wires 18 to form the plugging column 11 of the left atrial appendage occluder. Therefore, the number of the anchors 12 is not limited, a plurality of anchors can be provided, so that after the left atrial appendage occluder is implanted in a human body, a pressure of the tip of the anchor 12 is smaller, the damage to the left atrial appendage is smaller, and the fitting property between the left atrial appendage occluder and the left atrial appendage is improved. Furthermore, the plugging column 11 is formed by weaving a plurality of metal wires 18, so that the supporting force of the plugging column 11 is improved while the number of the anchors 12 is effectively increased, and thus the structural strength of the left atrial appendage occluder is ensured to meet the actual demand.

Figure 3:
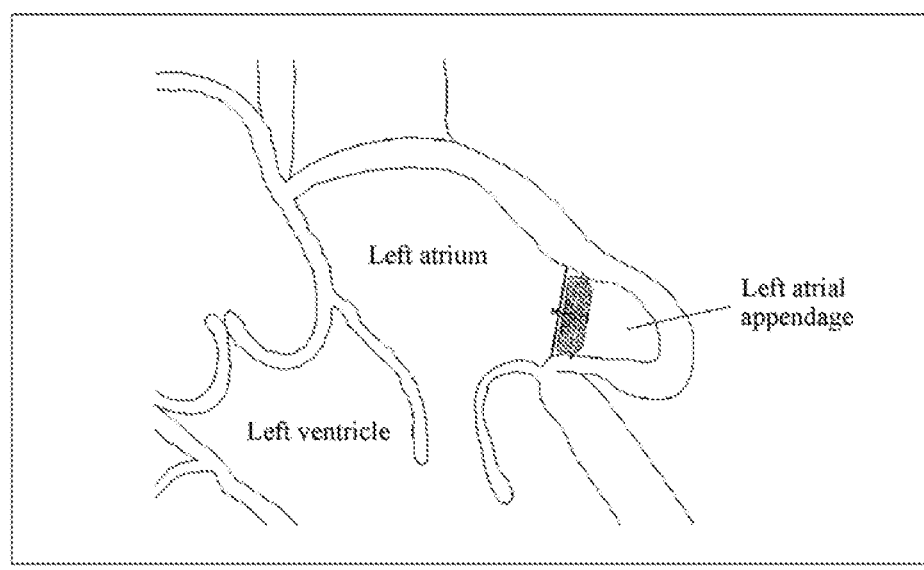
FIG. 3 is a state diagram after the left atrial appendage occluder according to the first embodiment is implanted into left atrial appendage.

Further, as shown in FIG. 3 to FIG. 5, the tip of the anchor 12 is smoothly transitioned, and forms an anchoring portion 123 to attach in an inner wall of the left atrial appendage. The elastic metal wire 18 is laser-cutting to form an cutting groove 125. The anchor 12 is bent and extends from a proximal end of the cutting groove 125, and the tip of the anchor 12 faces a proximal end of the left atrial appendage occluder. In other words, the anchoring portion 123 faces the proximal end of the left atrial appendage occluder, so that a curved portion 124 having a smaller curvature is formed on the bottom end of the anchor 12, and the anchor 12 is connected to the flattened surface 61 by using the curved portion 124 as a transitional bend.

Figure 6:
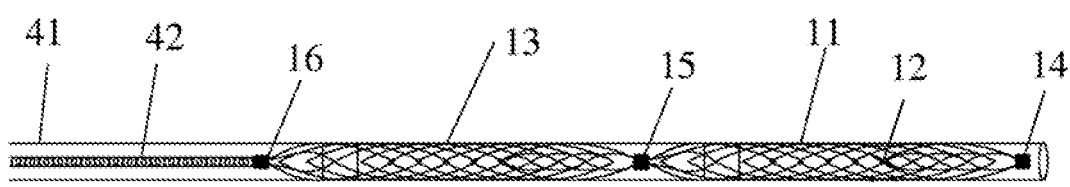
FIG. 6 is a state diagram after the left atrial appendage occluder according to the first embodiment is completely collected into a sheath.

The specific operations for pulling the left atrial appendage occluder 10 in the first embodiment into a sheath 41 of a delivery system are as follows: the delivery system comprises the sheath 41 and a push rod 42, wherein the push rod 42 runs in the sheath 41 and is removable. The push rod 42 may employ a thin rod member or a steel cable or the like. A distal end of the push rod 42 is connected to a proximal end of the left atrial appendage occluder 10. As shown in FIG. 6, the push rod 42 is pulled such that the push rod 42 moves towards an operator, and the left atrial appendage occluder 10 is driven by the push rod 42 to move towards the operator synchronously until the left atrial appendage occluder 10 is completely pulled into the sheath 41 of the delivery system. During the process of gradually pulling the left atrial appendage occluder 10 into the sheath 41, the proximal end of the plugging column 11 firstly enters the sheath 41 along with the push rod 42, and thereafter, the plugging column 11 begins to deform from the proximal end to the distal end and is gradually stretched into a straight line. At the same time, when the sheath 41 restrains the plugging column 11, the anchor 12 on the plugging column 11 is also deformed and stretched into a straight line, the anchor 12 is smoothly deformed in a direction in which the plugging column 11 is pulled into the sheath 41 to a shape after laser-cutting, therefore, the deformation of the bottom end of the anchor 12 is very small; and finally, the distal end of the plugging column 11 enters the sheath 41 along with the push rod 42 at last, so that the left atrial appendage occluder is finally received in the sheath 41 of the delivery system in a linear state.

Figure 7:
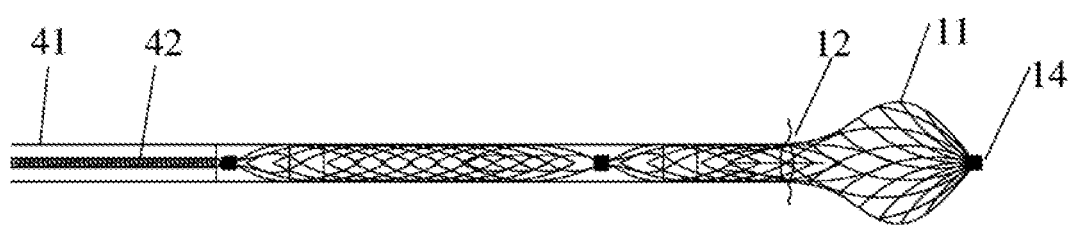
FIG. 7 is a state diagram in which a small portion of the anchors on the left atrial appendage occluder according to the first embodiment are released from the sheath.
Figure 8:
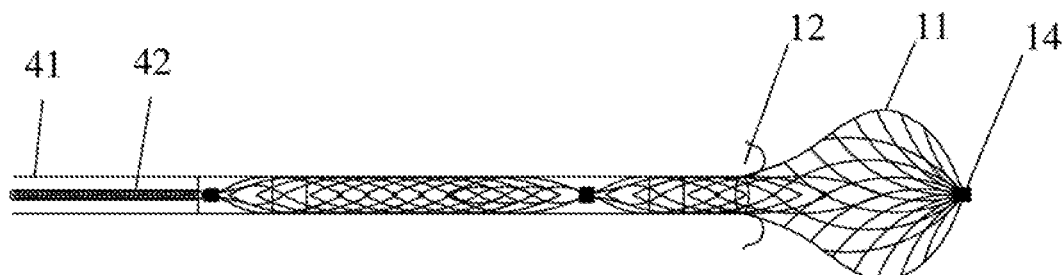
FIG. 8 is a state diagram in which a large portion of the anchors on the left atrial appendage occluder according to the first embodiment are released from the sheath.
Figure 9:
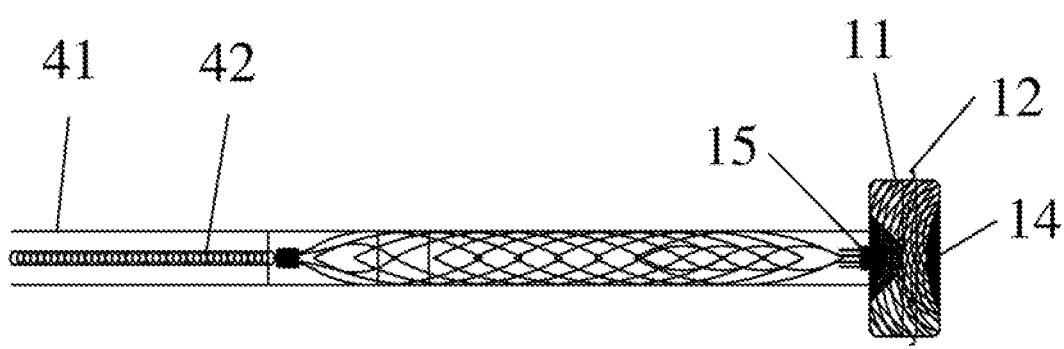
FIG. 9 is a state diagram in which the column on the left atrial appendage occluder according to the first embodiment is completely released from the sheath.

The specific operations for implanting the left atrial appendage occluder 10 in the first embodiment into left atrial appendage of a patient by using a delivery system are as follows: as shown in FIG. 7 to FIG. 9, when the push rod 42 is connected to the proximal end of the left atrial appendage occluder 10, the push rod 42 is pushed such that the push rod 42 moves away from the operator, and the left atrial appendage occluder 10 is driven by the push rod 42 to move away from the operator synchronously until the left atrial appendage occluder 10 is completely released from the sheath 41 of the delivery system. During the process of gradually releasing the left atrial appendage occluder 10 from the sheath 41, as shown in FIG. 7, the distal end of the plugging column 11 is firstly released from the sheath 41, and under the action of resilience force of the elastic metal wire 18 per se, a distal end releasing portion of the plugging column 11 is restored from a straight line shape to its preset expanded shape (that is, the initial expanded shape when not being collected into the sheath 41). Thereafter, as shown in FIG. 8, the anchor 12 on the plugging column 11 is also released from the sheath 41, wherein the anchor 12 is formed by partially flattening and laser-cutting the elastic metal wire 18, so that the anchor 12 is restored from a straight line shape to its preset expanded shape under the action of its resilience force. Finally, the proximal end of the plugging column 11 is released from the sheath 41 at last, under the action of resilience force of the elastic metal wire 18, the proximal end releasing portion of the plugging column 11 is restored from a straight line shape to its preset expanded shape. In this case, the plugging column 11 is completely released from the sheath 41 and wholly restored to its preset expanded shape, and the anchoring portion 123 of the tip of the anchor 12 is anchored on the inner wall of the left atrial appendage, as shown in FIG. 3. Therefore, the left atrial appendage occluder is implanted by attaching to the inner wall of the left atrial appendage, and the left atrial appendage is occluded.

In the left atrial appendage occluder 10 according to the first embodiment, the anchor 12 is pre-formed on the first elastic metal wire, and then the first elastic metal wire and a second elastic metal wire are woven into the plugging column 11 and the anchor 12 is located on the peripheral surface of the plugging column 11. Therefore, the anchor 12 and the plugging column 11 are integrally formed, the firmness of the anchor 12 is very good, and the anchor 12 is not likely to fall from the plugging column 11, so that the left atrial appendage occluder 10 can be firmly and reliably attached to the inner wall of the left atrial appendage. Further, the anchor 12 is formed by partially flattening, laser-cutting, heat-treating and setting the elastic metal wire 18, so that the anchor 12 is in the shape of a sheet which is consistent with the flattened surface 61 of the elastic metal wire 18. The anchor 12 is relatively soft and thin, and the anchor 12 and the flattened surface 61 of the elastic metal wire 18 (that is, the anchor 12 and the plugging column 11)

are connected by using the curved portion 124 of the bottom end of the anchor 12 as a curved transitional bend. At the same time, when the left atrial appendage occluder is pulled into the sheath 41 by the delivery system, a bending direction of deformation of the anchor 12 is opposite to an overall bending direction for forming the anchor 12 when the anchor 12 is formed on the elastic metal wire 18, that is, the anchor 12 is bent and extends from the proximal end of the cutting groove 125, and the tip of the anchor 12 faces the proximal end of the left atrial appendage occluder. Therefore, during the process of pulling the left atrial appendage occluder 10 into the sheath 41, the anchor 12 is smoothly stretched and deformed to a straight line in the direction of pulling the left atrial appendage occluder 10, and is attached into the cutting groove 125 of the flattened surface 61 of the elastic metal wire 18. Therefore, the deformation of a bending place between the anchor 12 and the plugging column 11 (that is, the bottom end of the anchor 12) is very small, so that after the left atrial appendage occluder 10 is released from the sheath 41, the anchor 12 can be thoroughly restored to its preset expanded shape. Thus, the plugging column 11 can withstand repeated stretching for a plurality of times, so that the left atrial appendage occluder 10 can be repeatedly collected into the sheath 41 and released from the sheath 41 for a plurality of times. Finally, according to this application, the left atrial appendage occluder 10 is repeatedly released from and collected into the sheath 41 of the delivery device for a plurality of times under the premise that the left atrial appendage occluder 10 can be firmly and stably fixed on the inner wall of the left atrial appendage.

More specifically, the left atrial appendage occluder 10 having the woven structure according to this application is compared with a cage-type left atrial appendage occluder in the prior art, referring to FIG. 20. FIG. 20a and FIG. 20b are schematic structural diagrams of a anchor 200 on the cage-type left atrial appendage occluder in the prior art in an initial state and being collected into a sheath, respectively. It can be seen from FIG. 20a and FIG. 20b that after the cage-type left atrial appendage occluder in the prior art is collected into the sheath, a bending angle of a bottom end of a anchor 100 (that is, a connecting end of the anchor 100 and a cage 200) is as large as about 95°. FIG. 20c and FIG. 20d are schematic structural diagrams of a anchor 12 on the left atrial appendage occluder 10 according to this application in an initial state and being collected into a sheath, respectively. It can be seen from FIG. 20c and FIG. 20d that after the left atrial appendage occluder 10 according to this application is collected into the sheath, a bending angle of the bottom end of the anchor 12 (that is, a connecting end of the anchor 12 and the plugging column 11) is as small as about 19°. Compared with the cage-type left atrial appendage occluder in the prior art, the bending angle of the bottom end of the anchor 12 according to this application is very small.

Further, refer to FIG. 21 to FIG. 24. FIG. 21a and FIG. 21b are diagrams of the left atrial appendage occluder 10 not being collected into the sheath 41 according to this application and the cage-type left atrial appendage occluder in the prior art, respectively. It can be seen from FIG. 21a and FIG. 21b that, the tip of the anchor 12 on the left atrial appendage occluder 10 according to this application and the tip of the anchor 100 on the cage-type left atrial appendage occluder in the prior art both face the proximal end of the left atrial appendage occluder. FIG. 22a and FIG. 22b are diagrams of the left atrial appendage occluder 10 being partially collected into the sheath 41 according to this application and the cage-type left atrial appendage occluder in the prior art, respectively. FIG. 23a and FIG. 23b are diagrams of the left atrial appendage occluder 10 being completely collected into the sheath 41 according to this application and the cage-type left atrial appendage occluder in the prior art, respectively. It can be seen from FIG. 22 and FIG. 23 that, the anchor 12 on the left atrial appendage occluder 10 according to this application is deformed in the direction of collecting the left atrial appendage occluder 10 into the sheath 41 and attached to the plugging column 11, so that the deformation of the bottom end of the anchor 12 is very small. However, the anchor 100 on the cage-type left atrial appendage occluder in the prior art is deformed opposite to the direction of collecting the cage-type left atrial appendage occluder into the sheath 41, and attached to the cage 200, so that the deformation of the bottom end of the anchor 200 is very large. FIG. 24a and FIG. 24b are diagrams of the left atrial appendage occluder 10 being completely collected into the sheath 41 according to this application and the cage-type left atrial appendage occluder in the prior art, respectively. It can be seen from FIG. 24a and FIG. 24b that after the left atrial appendage occluder 10 according to this application is released from the sheath 41, since the deformation of the bottom end of the anchor 12 is very small, the anchor 12 can be fully restored to its initial state, and the tip of the anchor 12 still faces the proximal end of the left atrial appendage occluder 10. Therefore, the left atrial appendage occluder 10 can still be fixed on the inner wall of the left atrial appendage through the anchor 12 to ensure that the left atrial appendage occluder 10 can be used normally. However, after the cage-type left atrial appendage occluder in the prior art is released from the sheath 41, since the deformation of the bottom end of the anchor 100 is very large, the anchor 100 cannot be restored to its initial state, the tip of the anchor 100 faces the distal end of the left atrial appendage occluder. Therefore, the anchor 100 loses the effect of fixing the cage-type left atrial appendage occluder on the inner wall of the left atrial appendage, and thus the cage-type left atrial appendage occluder cannot be reused. Thus, compared with the cage-type left atrial appendage occluder in the prior art, the left atrial appendage occluder 10 according to this application can be repeatedly pushed and pulled in the sheath 41.

Further, as shown in FIG. 2 and FIG. 5, the anchor 12 has a "C" shape, and has an opening 122. Selectively, the anchor 12 may have a "U" shape, and have an opening 122. The opening 122 of the anchor 12 faces the proximal end of the left atrial appendage occluder 10. During the process of pulling the left atrial appendage occluder into the sheath 41, the anchor 12 is unbent from the "C" shape to a straight line with the restraint of the sheath 41, and restored and attached to the flattened surface 61 of the elastic metal wire 18 on which the anchor 12 is located. The restored anchor 12 neither hinders the collection process of the left atrial appendage occluder 10, nor causes left atrial appendage injury due to dragging the left atrial appendage occluder 10. During the process of releasing the left atrial appendage occluder 10 from the delivery sheath 41, the anchor 12 gradually extends out of the delivery sheath 41 and restores the "C" shape, which further reduces the deformation amount of the bottom end of the anchor 12 during the process of pushing and pulling the left atrial appendage occluder 10. At the same time, the opening 122 of the anchor 12 faces the proximal end of the left atrial appendage occluder 10, so that the anchoring portion at the tip of the anchor 12 can be smoothly anchored on the inner wall of the left atrial appendage. Therefore, the effect of the anchor 12 is to anchor the relative position of the left atrial appendage occluder 10 in the left atrial appendage, so that the left atrial appendage occluder 10 is free of position offset under the heartbeat.

At present, the thickness of the inner wall of the left atrial appendage in the human body is generally about 3 mm to 4 mm. Therefore, in this application, the length of the anchor 12 is 1 mm to 4 mm, preferably 2 mm to 3 mm, so that the damage to the inner wall of the left atrial appendage is relatively small after the anchor 12 is fixed on the inner wall of the left atrial appendage. In addition, according to actual needs, the elastic force, the thickness, the position on the plugging column 11, and the bending angle of the anchor 12 all can be adjusted. Meanwhile, the angle, length, thickness and position of the anchoring portion 123 at the tip of the anchor 12 can also be adjusted.

Further, as shown in FIG. 2, the left atrial appendage occluder 10 has a two-stage segmented structure comprising the cover disk 13 located at an outlet of the left atrial appendage and the plugging column 11 located inside the left atrial appendage. The cover disk 13 has a flat disc structure woven from a plurality of elastic metal wires 18 without the anchor 12. The plugging column 11 has a cylindrical structure co-woven from a plurality of elastic metal wires 18 with the anchor 12 and a plurality of elastic metal wires 18 without the anchor 12, and is integrally formed. After being cut, a woven circular net is fixed by metal gathering points at two ends, placed into a molding die, heat-treated and set into a cylindrical structure. Preferably, the elastic metal wire 18 is a nickel-titanium alloy metal wire, and the superelasticity of the material is very good, so that the superelasticity of the cover disk 13 and the plugging column 11 is also good. Therefore, the left atrial appendage occluder has the superelastic property, so as to ensure that the left atrial appendage occluder can be fully restored to its preset expanded shape after being released from the sheath 41. The anchors 12 are evenly distributed on the peripheral surface of the plugging column 11, and the number of anchors 12 may be two or more. An inner wall of the cover disk 13 and an inner wall of the plugging column 11 are fixedly covered with one or more blood flow blocking membranes 17. The blood flow blocking membrane 17 is a polyester fiber membrane, and the blood flow blocking membrane 17 is flatly fixed in the cover disk 13 and the plugging column 11 and used for blocking blood flow. Anchors which fix the blood flow blocking membrane 17 and the cover disk 13 as well as the blood flow blocking membrane 17 and the plugging column 11 may be a suture made of a polyester material, so that the blood flow blocking membrane 17 and the cover disk 13 as well as the blood flow blocking membrane 17 and the plugging column 11 are both sutured and fixed. The cover disk 13 and the plugging column 11 are separately woven, therefore, a supporting force of the cover disk 13 and a supporting force of the plugging column 11 can be different due to different knitting tightness of the elastic metal wire 18 or different thickness of the elastic metal wire 18 or the like.

In addition, the left atrial appendage occluder further has three gathering points: a distal gathering point 14 located at the distal end of the plugging column 11, an intermediate gathering point 15 located between the plugging column 11 and the cover disk 13, and a proximal gathering point 16 located at the proximal end of the cover disk 13. The function of the three gathering points is to constrain and gather the woven elastic metal wires 18 to one point. Two ends of the plugging column 11 are constrained and fixed by the distal gathering point 14 and the intermediate gathering point 15 respectively, and two ends of the cover disk 13 are constrained and fixed by the intermediate gathering point 15 and the proximal gathering point 16 respectively. In other words, the metal gathering points of the proximal ends of a plurality of elastic metal wires 18 constituting the cover disk 13 are constrained and fixed by the proximal gathering point 16, the metal gathering points of the distal ends of the plurality of elastic metal wires 18 constituting the cover disk 13 and the metal gathering points of the proximal ends of a plurality of elastic metal wires 18 constituting the plugging column 11 are constrained and fixed by the intermediate gathering point 15, and the metal gathering points of the distal ends of the plurality of elastic metal wires 18 constituting the plugging column 11 are constrained and fixed by the distal gathering point 14. The function of the distal gathering point 14, the intermediate gathering point 15 and the proximal gathering point 16 is to constrain and gather the plurality of woven elastic metal wires 18 to one point. The distal gathering point 14, the intermediate gathering point 15 and the proximal gathering point 16 are all made of a metal tube, and the three are connected to the elastic metal wires 18 by using a same connection structure. The connection manner of the proximal gathering point 16 with the plurality of elastic metal wires 18 is described below.

Specifically, a connection manner 1 of the proximal gathering point 16 with the plurality of elastic metal wires 18 is as follows: as shown in FIG. 19, the proximal gathering point 16, the intermediate gathering point 15 and the distal gathering point 14 each comprise an inner steel sleeve 51 and an outer steel sleeve 52. End parts of the plurality of elastic metal wires 18 (that is, the metal gathering points of two ends of the cover disk 13 and the metal gathering points of two ends of the plugging column 11) are located in the inner steel sleeve 51, and are tightly matched and fixed with the inner steel sleeve 51. The inner steel sleeve 51 and the outer steel sleeve 52 are welded and fixed, thereby smoothly fixing the elastic metal wire 18 made of nickel-titanium alloy with the distal gathering point 14, the intermediate gathering point 15 and the proximal gathering point 16 made of stainless steel. An inner wall of a proximal end of the outer steel sleeve 52 of the proximal gathering point 16 is provided with internal connecting thread. The connecting thread is used for connecting the left atrial appendage occluder 10 and the push rod 42 in the delivery system, through which the left atrial appendage occluder can be effectively connected to or completely separated from the push rod 42.

A connection manner 2 of the proximal gathering point 16 with the plurality of elastic metal wires 18 is as follows: as shown in FIG. 25, likewise, the proximal gathering point 16, the intermediate gathering point 15 and the distal gathering point 14 each comprise an inner steel sleeve 51 and an outer steel sleeve 52. End parts of the plurality of elastic metal wires 18 (that is, the metal gathering points of two ends of the cover disk 13 and the metal gathering points of two ends of the plugging column 11) are located between the inner steel sleeve 51 and the outer steel sleeve 52, and the plurality of elastic metal wires 18 is tightly matched and fixed with the inner steel sleeve 51. The inner steel sleeve 51 and the outer steel sleeve 52 are welded and fixed, thereby smoothly fixing the elastic metal wire 18 made of nickel-titanium alloy with the distal gathering point 14, the intermediate gathering point 15 and the proximal gathering point 16 made of stainless steel. This is a preferred connection structure between the proximal gathering point 16 and the elastic metal wire 18, which can effectively shorten the axial length of the proximal gathering point 16, and reduce thrombosis and damage to left atrial appendage. The inner wall of the proximal end of the inner steel sleeve 51 of the proximal gathering point 16 is provided with a connecting thread, and thus the connecting thread is an internal thread. The connecting thread is used for connecting the left atrial appendage occluder 10 and the push rod 42 in the delivery system, through which the left atrial appendage occluder 10 can be effectively connected to or completely separated from the push rod 42.

Preferably, in the above two connection manners, the outer wall of the proximal end of the outer steel sleeve 52 of the proximal gathering point 16 has a frustum shape, and the diameter thereof gradually increases from the proximal end, thereby facilitating the smooth collection of the proximal gathering point 16 into the sheath 41.

Further, as shown in FIG. 2, the proximal end of the plugging column 11 is provided with a first region recessed inward, the intermediate gathering point 15 is embedded in the first region of the plugging column 11, and the proximal end of the intermediate gathering point 15 is located at a distal side of the proximal end of the plugging column 11. Therefore, the compressive strength of the plugging column 11 can be increased, the deformation amount of the plugging column 11 can be reduced, and the plugging column 11 can be closely attached to the cover disk 13, so that the spacing between the plugging column 11 and the cover disk 13 can be finely adjusted. In addition, the distal end of the plugging column 11 is also provided with a third region recessed inward, and the distal gathering point 14 is embedded in the third region of the plugging column 11, so that the intermediate gathering point 15 and the distal gathering point 14 at two ends of the plugging column 11 are both concave structures. Therefore, when the plugging column 11 is deformed, the plugging column 11 will be attached to the cover disk 13 to ensure the occlusion effect of the left atrial appendage occluder, and meanwhile the distal gathering point 14 of the left atrial appendage occluder would not break though the left atrial appendage after being recessed inward, thereby avoiding the damage to the left atrial appendage.

It can be seen from FIG. 6 to FIG. 9 that during the process of collecting the left atrial appendage occluder comprising the foregoing cover disk 13, the plugging column 11, the "C"-shaped anchor 12, the proximal gathering point 16, the intermediate gathering point 15 and the distal gathering point 14 into the sheath 41, a push cable matched with the sheath 41 is first connected to the proximal gathering point 16. During the process of pulling into the sheath 41, the proximal gathering point 16 first enters the sheath 41 along with the push cable, and then the shape of the cover disk 13 is gradually stretched from a disc to a straight line in the delivery sheath 41 and enters the sheath 41. After that, the intermediate gathering point 15 is pulled into the sheath 41, and then the plugging column 11 is also gradually stretched from a cylindrical shape to a straight line in the delivery sheath 41. The anchor 12 on the plugging column 11 is also smoothly stretched from a "C" shape to a straight line with the constraint of the sheath 41, and restored and attached to the flattened surface 61 of the elastic metal wire 18 on which the anchor 12 is located. At last, the distal gathering point 14 also enters the sheath 41. Finally, the entire left atrial appendage occluder will be collected into the delivery sheath 41 in the form of a straight line. The left atrial appendage occluder can still restore the preset expanded shape after being repeatedly collected into and released from the sheath 41. During the process of releasing the left atrial appendage occluder from the delivery sheath 41, the plugging column 11 and the cover disk 13 are sequentially and gradually expanded from a straight line, and finally restored to the preset expanded shape. The anchor 12 gradually extends from the delivery sheath 41 without hurting other heart tissue, and the anchor 1212 can withstand repeated stretching without breaking.

Second Embodiment

A left atrial appendage occluder 20 in the second embodiment differs from that in the first embodiment only in that the left atrial appendage occluder 20 according to the second embodiment employs partial laser-cutting and then heat-treatment setting on an elastic metal sheet 21 to form a anchor 12, and co-weaving of the elastic metal sheet 21 and an elastic metal wire 18 to form an integrally formed plugging column 11.

Figure 10:
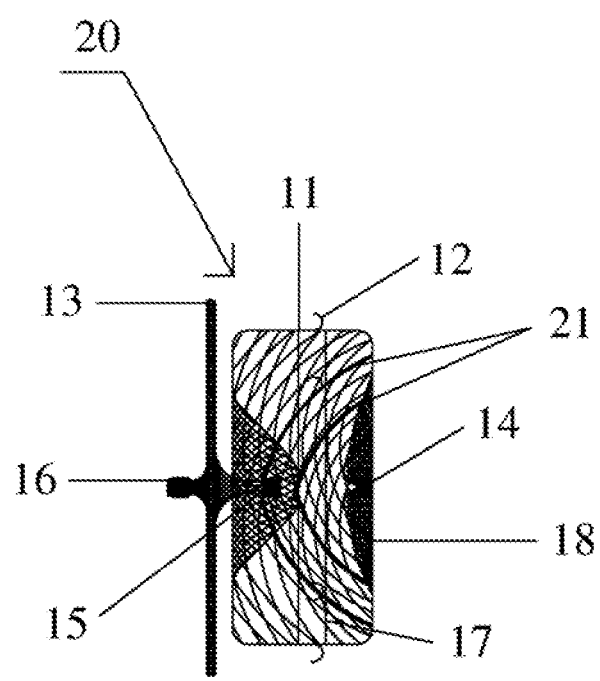
FIG. 10 is a front view of a second embodiment of a left atrial appendage occluder in the present invention.
Figure 11:
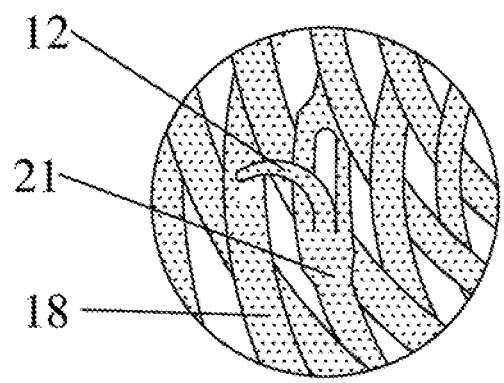
FIG. 11 is a partial enlarged view of a plugging column and a anchor on the left atrial appendage occluder according to the second embodiment.
Figure 12:
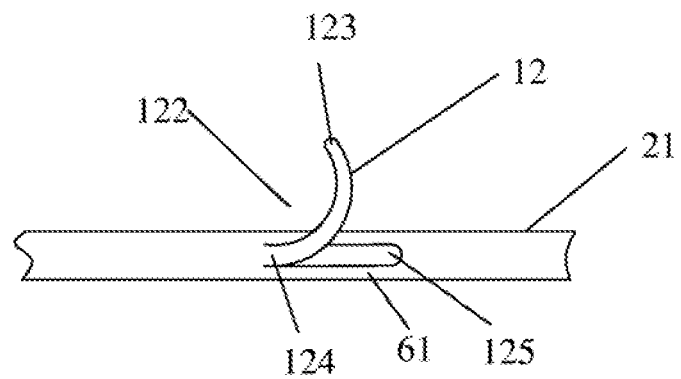
FIG. 12 is a state diagram of the anchor after an elastic metal sheet on the left atrial appendage occluder according to the second embodiment is subjected to laser-cutting.

Specifically, the left atrial appendage occluder 20 according to the second embodiment comprises the plugging column 11 having a proximal end and a distal end. Seen in a direction shown in FIG. 10, a left end of the plugging column 11 is the proximal end of the plugging column 11, and a right end of the plugging column 11 is the distal end of the plugging column 11. The plugging column 11 is woven from an elastic metal wire 18 and an elastic metal sheet 21, and the elastic metal sheet 21 has at least one flattened surface 61. The flattened surface 61 is provided with a anchor 12 bent and extending outwardly and formed on a peripheral surface of the plugging column 11. In other words, the anchor 12 is made by laser-cutting the elastic metal sheet 21, so that the peripheral surface of the plugging column 11 is provided with a plurality of anchors 12, the plurality of anchors 12 being used for anchoring the plugging column 11 on an inner wall of the left atrial appendage. As shown in FIG. 11 to FIG. 12, a tip of the anchor 12 is an anchoring portion 123 attached in the inner wall of the left atrial appendage, a bottom end of the anchor 12 is a curved portion 124, and the anchor 12 and the flattened surface 61 are connected by using the curved portion 124 as a transitional bend.

A fabricating method for the left atrial appendage occluder according to the second embodiment comprises the following steps in sequence:

a) laser-cutting an edge contour of a anchor 12 on one or more flat elastic metal sheets 21, the flat elastic metal sheet 21 forming a flattened surface 61;

b) bending the anchor 12 outward from the elastic metal sheet 21, wherein a tip of the anchor 12 has an anchoring portion 123, a bottom end of the anchor 12 has a curved portion 124, and the anchor 12 is connected to the flattened surface 61 by using the curved portion 124 as a transitional bend;

c) performing heat-treatment on the elastic metal sheet 21 to set the anchor 12;

d) weaving the elastic metal sheet 21 and a plurality of elastic metal wires 18 into the plugging column 11, and locating the anchor 12 on the peripheral surface of the plugging column 11; and e) placing the plugging column 11 into a molding die, and performing heat-treatment for setting, so as to set the plugging column 11.

Further, the structure of the left atrial appendage occluder 20 according to the second embodiment is substantially the same as that of the left atrial appendage occluder 10 according to the first embodiment. Therefore, the left atrial appendage occluder 20 according to the second embodiment is also a two-stage segmented structure comprising a cover disk 13 and the plugging column 11. The cover disk 13 is woven from a plurality of elastic metal wires 18 without a anchor 12, and the plugging column 11 is co-woven from a plurality of elastic metal sheets 21 with the anchor 12 and a plurality of elastic metal wires 18 without the anchor 12, and is integrally formed. After being cut, a woven circular net is fixed by metal gathering points at two ends, placed into a molding die, heat-treated and set into a cylindrical structure. The elastic metal sheet 21 is a nickel-titanium alloy elastic metal sheet 21, so that the left atrial appendage occluder 20 has the superelastic property. The elastic metal sheet 21 is laser-cutting to form an cutting groove 125. The anchor 12 is bent and extends from a proximal end of the cutting groove 125, and a tip of the anchor 12 faces a proximal end of the left atrial appendage occluder. The anchor 12 has a "C" shape or a "U" shape, and has an opening 122. The opening 122 of the anchor 12 faces the proximal end of the left atrial appendage occluder 20. An inner wall of the cover disk 13 and an inner wall of the plugging column 11 are fixedly covered with one or more blood flow blocking membranes 17. The blood flow blocking membrane 17 is flatly fixed in the cover disk 13 and the plugging column 11, and used for blocking blood flow. During the process of collecting the left atrial appendage occluder into a sheath tube 41 and releasing the left atrial appendage occluder from the sheath tube 41, the elastic metal sheet 21 is regularly folded or unfolded. During the process of collecting into the sheath 41, the anchor 12 cutting on the elastic metal sheet 21 is restored to the state before the cutting, that is, the anchor 12 is flatly attached to the elastic metal sheet 21. During the release process, the anchor 12 gradually extends out of the sheath 41 to restore the initial shape. There may be one or more elastic metal sheets 21 distributed on the plugging column 11. The process for processing the anchor 12 on the elastic metal sheet 21 is simple, and the mechanical properties of the processed elastic metal sheet 21 and the anchor 12 are stable and reliable.

Third Embodiment

Figure 13:
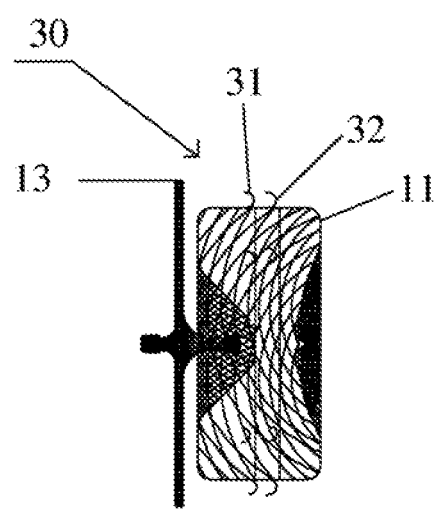
FIG. 13 is a front view of a third embodiment of a left atrial appendage occluder in the present invention.

As shown in FIG. 13, the left atrial appendage occluder 30 according to the third embodiment also comprises a plugging column 11, a cover disk 13, a distal gathering point 14, an intermediate gathering point 15, a proximal gathering point 16, a blood flow blocking membrane 17 and anchors 12. The anchors 12 are distributed on the plugging column 11 in two or more rows, that is, the anchors 12 comprise one or more rows of proximal anchors 31, and one or more rows of distal anchors 32. The proximal anchor 31 and the distal anchor 32 both are made by partially forging and then laser-cutting an elastic metal wire 18 or made by laser-cutting an elastic metal sheet 21. The proximal anchor 31 and the distal anchor 32 are evenly distributed on the plugging column 11, the proximal anchor 31 is close to the intermediate gathering point 15, and the distal anchor 32 is close to the distal gathering point 14. When the left atrial appendage occluder is released from a sheath 41, the distal anchor 32 first extends out of the sheath 41, and the left atrial appendage occluder is pre-fixed in the left atrial appendage, so that the release process for the remaining part is stable without shaking. After the proximal anchor 31 is released, the stability of the left atrial appendage occluder in the left atrial appendage would increase. The number of proximal anchors 31 may be two or more, and the number of distal anchors 32 may also be two or more.

Fourth Embodiment

Figure 14:
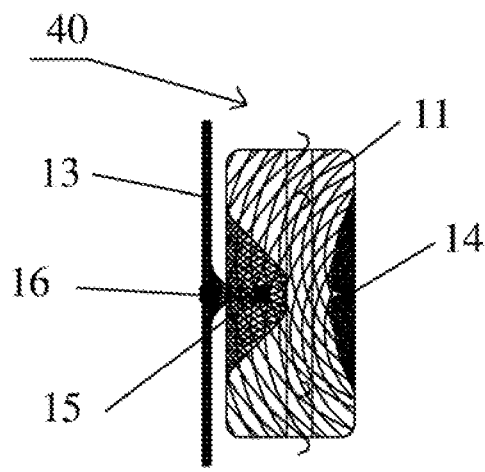
FIG. 14 is a front view of a fourth embodiment of a left atrial appendage occluder in the present invention.
Figure 15:
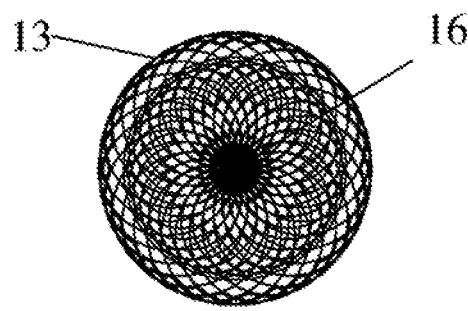
FIG. 15 is a bottom view of the fourth embodiment of the left atrial appendage occluder in the present invention.
Figure 16:
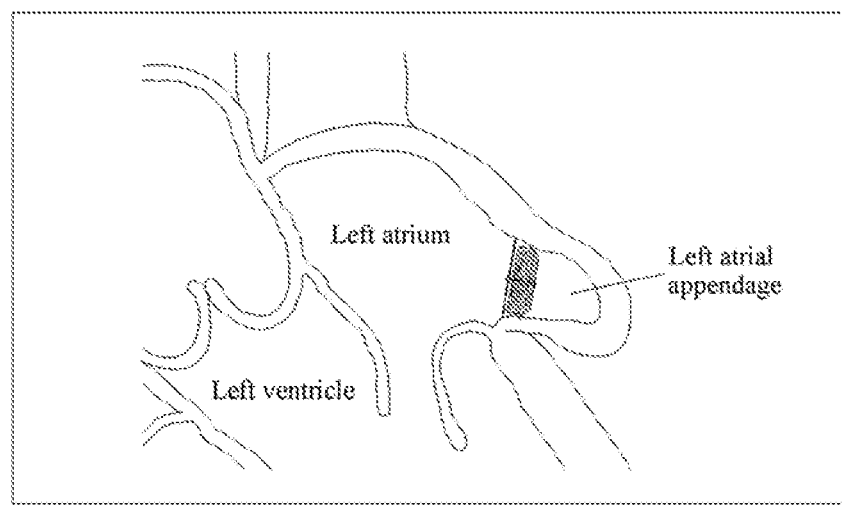
FIG. 16 is a state diagram after the left atrial appendage occluder according to the fourth embodiment is implanted into left atrial appendage.

As shown in FIG. 14 to FIG. 16, a left atrial appendage occluder 40 according to the fourth embodiment comprises a plugging column 11, a anchor 12, a cover disk 13, a distal gathering point 14, an intermediate gathering point 15, a proximal gathering point 16, and a blood flow blocking membrane 17. Wherein, the proximal gathering point 16 is completely embedded in the cover disk 13 before heat-treatment setting, a tail end thereof (that is, a proximal end of the proximal gathering point 16) and the cover disk 13 are in one plane, and the two are flush. In other words, a proximal end of the cover disk 13 is provided with a second region recessed inward, the proximal gathering point 16 is embedded in the second region of the cover disk 13, and the proximal end of the proximal gathering point 16 is flush with the proximal end of the cover disk 13. With the foregoing structure, the left atrial appendage occluder 40 will be completely endothelialized after being implanted in a human body for 6 months, and the cover disk 13 will be covered by new endothelial tissue. The proximal gathering point 16 is flush with the cover disk 13, so that the tissue after endothelialization of the left atrial appendage occluder 40 is flat in surface, reducing the risk of re-thrombosis. In addition, the flat cover disk 13 also reduces the probability of thrombosis before the left atrial appendage occluder 40 is completely endothelialized.

In the left atrial appendage occluder 40 according to the fourth embodiment, the proximal gathering point 16 is connected to proximal ends of a plurality of elastic metal wires 18 woven into the cover disk 13 in the following manner. As shown in FIG. 26, the proximal gathering point 16 also comprises an inner steel sleeve 51 and an outer steel sleeve 52. The proximal ends of the plurality of elastic metal wires 18 are located between the inner steel sleeve 51 and the outer steel sleeve 52. The plurality of elastic metal wires 18 are tightly matched and fixed with the inner steel sleeve 51. Meanwhile, the proximal ends of the plurality of elastic metal wires 18 extend from the proximal end of the proximal gathering point 16 into a space between the inner steel sleeve 51 and the outer steel sleeve 52, so that the proximal gathering point 16 is completely embedded in the cover disk 13 or flush with the cover disk 13. After that, the inner steel sleeve 51 and the outer steel sleeve 52 are welded and fixed, thereby smoothly fixing the elastic metal wire 18 made of nickel-titanium alloy with the proximal gathering point 16 made of stainless steel. Preferably, an inner wall of the proximal end of the inner steel sleeve 51 of the proximal gathering point 16 is provided with a connecting thread. The connecting thread is used for connecting the left atrial appendage occluder 40 and a push rod 42 in a delivery system, through which the left atrial appendage occluder 40 can be effectively connected to or completely separated from the push rod 42.

Fifth Embodiment

Figure 17:
FIG. 17 is a schematic structural diagram of a anchor in a fifth embodiment of a left atrial appendage occluder in the present invention.
Figure 18:
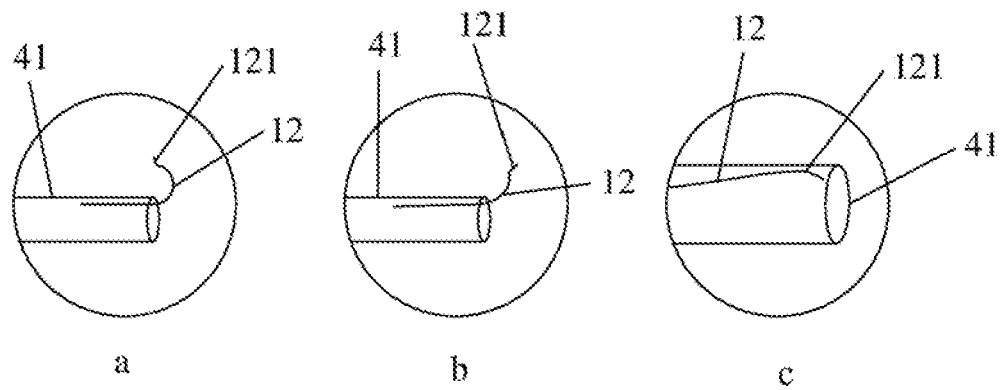
FIG. 18 is a state diagram during the process of collecting the left atrial appendage occluder according to the fifth embodiment into the sheath; wherein a) is a state diagram when the anchor in the left atrial appendage occluder according to the fifth embodiment is not collected into the sheath.

A left atrial appendage occluder 50 according to the fifth embodiment comprises a plugging column 11, a anchor 12, a cover disk 13, a distal gathering point 14, an intermediate gathering point 15, a proximal gathering point 16, and a blood flow blocking membrane 17. Wherein, as shown in FIG. 17, a tip of the anchor 12 is further provided with a drag reducing hook portion 121. After the left atrial appendage occluder 50 is collected into a delivery system, as shown in FIG. 18, the drag reducing hook portion 121 of the anchor 12 is in line contact with an inner wall of a sheath 41 in the delivery system, thereby reducing a contact area between the anchor 12 and the inner wall of the sheath 41, further reducing resistance when the left atrial appendage occluder is pushed out of the sheath 41, and also preventing the damage to a wall of the sheath 41 by an anchoring portion 123 at the tip of the anchor 12 in the left atrial appendage occluder 50, so that the objective of repeatedly pushing and pulling the left atrial appendage occluder 50 by using the delivery system can be achieved.

In summary, the present invention effectively overcomes various shortcomings in the prior art and has high industrial utilization value.

The above-described embodiments are merely illustrative of the principles and effects of the present invention, and are not intended to limit the present invention. Modifications or variations may be made to the embodiments by those skilled in the art without departing from the spirit and scope of the present invention. Therefore, all equivalent modifications or changes made by those skilled in the art without departing from the spirit and technical idea disclosed in the present invention are stilled covered by the appended claims of the present invention.

What is claimed is:

1. A left atrial appendage occluder comprising:
    a plugging column (11), anchors (12) located on the plugging column (11), a cover disk (13) and a blood flow blocking membrane (17) for blocking blood flow;
    the plugging column (11) is woven from elastic metal wires (18), a part of the elastic metal wires (18) of the plugging column (11) each has a flattening segment by partially flatting;
    the anchors (12) are made by cutting grooves (125) in the flattening segments of the plugging column (11), each of the anchors (12) has a shape of a sheet and is bent and extended from a proximal end of the cutting grooves (125) respectively, a tip of the each anchor points toward a proximal end of the left atrial appendage occluder;
    when the left atrial appendage occluder is constrained within a delivery system, the anchors are located on a peripheral surface of the plugging column (11), the tips of the anchors point toward a distal end of the left atrial appendage occluder and fit in the cutting grooves (125) respectively;
    the cover disk (13) is woven from the elastic metal wires (18), the cover disk (13) is connected to the plugging column (11);
    an inner wall of the cover disk (13) and an inner wall of the plugging column (11) are fixedly covered with one or more blood flow blocking membranes (17);
    the plugging column (11) is cylindrical, two ends of the plugging column (11) are respectively constrained and fixed by a distal gathering point (14) and an intermediate gathering point (15);
    the cover disk (13) is a flat disc, two ends of the cover disk (13) are respectively constrained and fixed by the intermediate gathering point (15) and a proximal gathering point (16);
    the proximal gathering point (16), the intermediate gathering point (15) and the distal gathering point (14) each comprises an inner steel sleeve (51) and an outer steel sleeve (52); and
    wherein two end parts of the elastic metal wires (18) constituting the cover disk (13) are fixed in the inner steel sleeves (51) of the proximal gathering point (16) and the intermediate gathering point (15) respectively, and two end parts of the elastic metal wires (18) constituting the plugging column (11) are fixed in the inner steel sleeves (51) of the intermediate gathering point (15) and the distal gathering point (14) respectively; or
    wherein two end parts of the elastic metal wires (18) constituting the cover disk (13) are fixed between the inner steel sleeves (51) and outer steel sleeves (52) of the proximal gathering point (16) and the intermediate gathering point (15) respectively, and two end parts of the elastic metal wires (18) constituting the plugging column (11) are fixed between the inner steel sleeves (51) and outer steel sleeves (52) of the intermediate gathering point (15) and the distal gathering point (14) respectively.

2. The left atrial appendage occluder as in claim 1, wherein the cutting grooves (125) are made by laser-cutting.

3. The left atrial appendage occluder as in claim 2, wherein a length of the anchors (12) ranges from 1 mm to 4 mm.

4. The left atrial appendage occluder as in claim 2, wherein each tip of the anchors (12) is further provided with a drag reducing hook portion (121); and when the left atrial appendage occluder is collected into the delivery system, the drag reducing hook portions (121) of the tips of the anchors (12) are in line contact with an inner wall of a sheath (41) in the delivery system.

5. The left atrial appendage occluder as in claim 1, wherein a length of the anchors (12) ranges from 1 mm to 4 mm.

6. The left atrial appendage occluder as in claim 1, wherein each tip of the anchors (12) is further provided with a drag reducing hook portion (121); and when the left atrial appendage occluder is collected into the delivery system, the drag reducing hook portions (121) of the tips of the anchors (12) are in line contact with an inner wall of a sheath (41) in the delivery system.

7. The left atrial appendage occluder as in claim 1, wherein the elastic metal wires (18) are nickel-titanium alloy metal wires.

8. The left atrial appendage occluder as in claim 1, wherein an inner wall of a proximal end of the inner steel sleeve (51) of the proximal gathering point (16) or an inner wall of a proximal end of the outer steel sleeve (52) of the proximal gathering point (16) is provided with a connecting thread, and the connecting thread is used for connecting the left atrial appendage occluder and a push rod (42) in the delivery system.

9. The left atrial appendage occluder as in claim 1, wherein an outer wall of a proximal end of the outer steel sleeve (52) of the proximal gathering point (16) has a frustum shape.

10. The left atrial appendage occluder as in claim 1, wherein a proximal end of the plugging column (11) is provided with a first region recessed inward, the intermediate gathering point (15) is embedded in the first region of the plugging column (11), and a proximal end of the intermediate gathering point (15) is located at a distal side of the proximal end of the plugging column (11).

11. The left atrial appendage occluder as in claim 1, wherein the proximal gathering point (16) is completely embedded in the cover disk (13), and a tail end of the proximal gathering point (16) is flush with a plane of the cover disk (13).

* * * * *